United States Patent
Wheatley et al.

(10) Patent No.: US 8,715,622 B2
(45) Date of Patent: May 6, 2014

(54) ECHOGENIC POLYMER MICROCAPSULES AND NANOCAPSULES AND METHODS FOR PRODUCTION AND USE THEREOF

(75) Inventors: Margaret A. Wheatley, Media, PA (US); Dalia El-Sherif, King of Prussia, PA (US)

(73) Assignee: Drexel University, Philadelphia, PA (US)

( * ) Notice: Subject to any disclaimer, the term of this patent is extended or adjusted under 35 U.S.C. 154(b) by 0 days.

(21) Appl. No.: 13/017,345

(22) Filed: Jan. 31, 2011

(65) Prior Publication Data

US 2011/0125079 A1   May 26, 2011

Related U.S. Application Data

(63) Continuation of application No. 10/472,430, filed as application No. PCT/US02/10260 on Apr. 1, 2002, now Pat. No. 7,897,141.

(60) Provisional application No. 60/280,412, filed on Mar. 30, 2001.

(51) Int. Cl.
| | |
|---|---|
| *A61B 8/00* | (2006.01) |
| *A61K 47/08* | (2006.01) |
| *A61K 47/18* | (2006.01) |
| *A61K 49/22* | (2006.01) |
| *G01N 29/04* | (2006.01) |

(52) U.S. Cl.
CPC ............ *A61K 47/08* (2013.01); *A61K 47/186* (2013.01); *A61K 49/223* (2013.01); *G01N 29/046* (2013.01)
USPC ........................................................ 424/9.5

(58) Field of Classification Search
None
See application file for complete search history.

(56) References Cited

U.S. PATENT DOCUMENTS

| | | |
|---|---|---|
| 5,585,112 A | 12/1996 | Unger et al. |
| 5,674,468 A | 10/1997 | Klaveness et al. |
| 5,676,925 A | 10/1997 | Klaveness et al. |
| 5,711,933 A | 1/1998 | Bichon et al. |
| 5,837,221 A | 11/1998 | Bernstein et al. |
| 5,853,698 A | 12/1998 | Straub et al. |
| 5,955,143 A | 9/1999 | Wheatley et al. |
| 6,080,429 A | 6/2000 | Cleland et al. |
| 6,139,818 A | 10/2000 | Bichon et al. |

OTHER PUBLICATIONS

Farnand et al. "Preparation of hollow spherical articles." 1979, Powder Technology 22:11-16.
Bjerknes et al., "Preparation of polymeric microbubbles:formulation studies and product characterisation", 1997, International Journal of Pharmaceutics 158:129-136.
Igartua et al., "Enhanced immune response after subcutaneous and oral immunization with biodegradable PLGA microspheres", 1998, Journal of Controlled Release 56:63-73.
Narayan et al., "Preparation and Characterization of Hollow Microcapsules for Use as Ultrasound Contrast Agents", Polymer Engineering and Science 1999 39(11):2242-2255.
Tachibana et al,, "Application of Ultrasound Energy as a New Drug Delivery System", 1999, Jpn. J. Appl. Phys. 38:3014-3019.

*Primary Examiner* — Michael G Hartley
*Assistant Examiner* — Melissa Perreira
(74) *Attorney, Agent, or Firm* — Saul Ewing LLP; Kathryn Doyle

(57) ABSTRACT

Methods for producing echogenic polymer microcapsules and nanocapsules for use in diagnostic imaging and delivery of bioactive compounds as well as targeted imaging and delivery to selected tissues and cells are provided. Compositions containing these echogenic polymer microcapsules and nanocapsules for use in diagnostic imaging and delivery of bioactive agents are also provided.

28 Claims, No Drawings

ECHOGENIC POLYMER MICROCAPSULES AND NANOCAPSULES AND METHODS FOR PRODUCTION AND USE THEREOF

CROSS-REFERENCE TO RELATED APPLICATIONS

The present application is a continuation of U.S. application Ser. No. 10/472,430, filed Apr. 9, 2004, now allowed, which is U.S. national phase application filed under 35 U.S.C. §371 claiming benefit to International Patent Application No. PCT/US02/10260, filed Apr. 1, 2002, which is entitled to priority under 35 U.S.C. §119(e) to U.S. Provisional Application No. 60/280,412, filed on Mar. 30, 2001, which applications are incorporated by reference herein in their entireties.

BACKGROUND OF THE INVENTION

Ultrasound contrast agents are used routinely in medical diagnostic, as well as industrial, ultrasound. For medical diagnostic purposes, contrast agents are usually gas bubbles, which derive their contrast properties from the large acoustic impedance mismatch between blood and the gas contained therein. Important parameters for the contrast agent include particle size, imaging frequency, density, compressibility, particle behavior (surface tension, internal pressure, bubble-like qualities), and biodistribution and tolerance.

Gas-filled particles are by far the best reflectors. Various bubble-based suspensions with diameters in the 1 to 15 micron range have been developed for use as ultrasound contrast agents. Bubbles of these dimensions have resonance frequencies in the diagnostic ultrasonic range, thus improving their backscatter enhancement capabilities. Sonication has been found to be a reliable and reproducible technique for preparing standardized echo contrast agent solutions containing uniformly small microbubbles. Bubbles generated with this technique typically range in size from 1 to 15 microns in diameter with a mean bubble diameter of 6 microns (Keller et al. 1986. *J. Ultrasound Med.* 5:493-498). However, the durability of these bubbles in the blood stream has been found to be limited and research continues into new methods for production of microbubbles. Research has also focused on production of hollow microparticles for use as contrast agents wherein the microparticle can be filled with gas and used in ultrasound imaging. These hollow microparticles, however, also have uses as drug delivery agents when associated with drug products. These hollow microparticles can also be associated with an agent which targets selected cells and/or tissues to produce targeted contrast agents and/or targeted drug delivery agents.

Surfactant stabilized microbubble mixtures for use as ultrasound contrast agents are disclosed in U.S. Pat. No. 5,352,436.

WO 9847540 discloses a contrast agent for diagnostic ultrasound and targeted disease imaging and drug delivery comprising a dispersion of a biocompatible azeotropic mixture, which contains a halocarbon.

WO 9421301 discloses an ultrasound agent consisting of a biocompatible oil-in-water emulsion in which the oil phase comprises an oil-soluble gas/fluid or gas precursor.

U.S. Pat. No. 5,637,289, U.S. Pat. No. 5,648,062, U.S. Pat. No. 5,827,502 and U.S. Pat. No. 5,614,169 disclose contrast agents comprising water-soluble, microbubble generating carbohydrate microparticles, admixed with at least 20% of a non-surface active, less water-soluble material, a surfactant or an amphiphillic organic acid. The agent is prepared by dry mixing, or by mixing solutions of components followed by evaporation and micronizing.

U.S. Pat. No. 5,648,095 discloses hollow microcapsules for use in imaging and drug delivery. The hollow microcapsules are made by combining a volatile oil, with an aqueous phase including a water soluble material such as starch or a polyethylene glycol conjugate to form a primary emulsion. The primary emulsion then is combined with a second oil to form a secondary emulsion, which is hardened and allows for microcapsules to form around a liquid core of the volatile oil. The volatile oil is then, removed by evaporation leaving a hollow microcapsule.

U.S. Pat. No. 5,955,143 discloses hollow polymer microcapsules that are produced by dissolving a film-forming polymer in a volatile non-aqueous solvent, dispersing into the polymer solution finely divided particles of a volatilizable solid core material, inducing formation of a solid polymer coating on the particulate solid core material to produce polymer microcapsules having an encapsulated solid core. This core is then removed to result in hollow microcapsules that can be then filled with gas for contrast imaging.

There remains a need for methods of production of biocompatible, biodegradable echogenic microcapsules and nanocapsules of a reproducible size range that can be used for contrast imaging and/or drug delivery with or without targeting capabilities.

SUMMARY OF THE INVENTION

An object of the present invention is to provide methods for producing echogenic polymer microcapsules and nanocapsules which comprise dissolving a non-water soluble substance which dissolves in a non-polar solvent and sublimes from the solid state, in one or more volatile non-polar solvents to form a first mixture; dissolving a polymer in said first mixture to form a second mixture; emulsifying the second mixture with or without water to produce a first population of microcapsules comprising the polymer and the non-water soluble substance; mixing said first population of microcapsules with a surfactant solution and stirring/homogenizing to break apart the first population of microcapsules and form a second population of microcapsules and/or nanocapsules that are smaller in size; hardening said second population of microcapsules and/or nanocapsules with a solvent; and washing and preferably freeze drying said second population of microcapsules and/or nanocapsules to remove excess non-water soluble substance from said second population of microcapsules and/or nanocapsules.

Alternatively, wherein the emulsification step of the second mixture produced in these methods is performed with water, the method may further comprise addition of a substance which dissolves in water and sublimes.

Another object of the present invention is to provide echogenic polymer microcapsules and nanocapsules produced in accordance with the methods of the present invention.

Another object of the present invention is to provide a contrast agent for diagnostic imaging in a subject which comprises echogenic polymer microcapsules and/or nanocapsules of the present invention that are filled with a gas. Such contrast agents may further comprise a targeting agent such as a peptide or antibody on the microcapsule and/or nanocapsule surface for targeting of the contrast agents to selected tissues or cells. Attachment of a targeting agent selective to a diseased tissue provides for a contrast agent which distinguishes between diseased and normal tissue. Use of contrast agents comprising echogenic polymer nanocapsules of the present invention permits imaging of tissues via access to locations of the vasculature too narrow for access via microcapsules, e.g. leaky tumor vasculature.

Another object of the present invention is to provide methods for imaging a tissue or tissues in a subject via administration of a contrast agent comprising echogenic polymer microcapsules and/or nanocapsules of the present invention that are filled with a gas. Contrast agents used in this method may further comprise a targeting agent such as a peptide or antibody on the microcapsule and/or nanocapsule surface for targeted delivery of the contrast agent to the selected tissue or tissues. Attachment of a targeting agent selective to a diseased tissue provides for a method of distinguishing via selective imaging diseased tissue from normal tissue. Similarly, attachment of a targeting agent selective to a malignant tissues provides for a method of distinguishing via selective imaging malignant tissue from benign tissue.

Another object of the present invention is to provide a composition for delivery of a bioactive agent which comprises a bioactive agent adsorbed to, attached to, and/or encapsulated in, or any combination thereof, echogenic polymer microcapsules and/or nanocapsules of the present invention. Such compositions may further comprise a targeting agent such as a peptide or antibody on the microcapsule and/or nanocapsule surface for targeting of the bioactive agent to selected tissues or cells. Attachment of a targeting agent selective to a diseased tissue provides for a delivery agent which delivers a bioactive agent selectively to diseased tissue. The bioactive agent can be released from the microcapsule and/or nanocapsule by exposure to ultrasound and/or upon degradation of the polymer capsule. Use of compositions comprising echogenic polymer nanocapsules of the present invention permits delivery of bioactive agents to locations of the vasculature too narrow for access via microcapsules, e.g. leaky tumor vasculature.

Yet another object of the present invention is to provide methods for delivery of bioactive agents to a subject via administration of a composition comprising bioactive agent adsorbed to, attached to, and/or encapsulated in, or any combination thereof, echogenic polymer microcapsules and/or nanocapsules of the present invention. Compositions used in this method may further comprise a targeting agent such as a peptide or antibody on the echogenic polymer microcapsule and/or nanocapsule surface for targeting of the bioactive agent to selected tissues or cells in the subject. In this method, bioactive agent is released from the microcapsule and/or nanocapsule by exposure to ultrasound, degradation of the polymer capsule or a combination thereof.

DETAILED DESCRIPTION OF THE INVENTION

The present invention relates to echogenic polymer microcapsules and nanocapsules and methods for producing such for use as contrast agents in diagnostic imaging and compositions for delivery of bioactive agents. The present invention further relates to attachment of a targeting agent to the echogenic polymer microcapsules and nanocapsules of the contrast agents and compositions for delivery of bioactive agents of the present invention for targeted diagnostic imaging and delivery of bioactive agents to a selected tissue or tissues. Production of echogenic polymer nanocapsules in accordance with the present invention permits imaging and delivery of bioactive agents to regions of the vasculature too narrow for access via microcapsules.

For purposes of the present invention, by "echogenic" it is meant that the microcapsule or nanocapsule is capable of producing a detectable echo when insonated with ultrasonic waves due to an acoustic impedance mismatch between blood and the microcapsule or nanocapsule. In a preferred embodiment, echogenic characteristics result from the microcapsule and/or nanocapsule being hollow and/or porous. By "porous" for purposes of the present invention, it is meant that the capsules contain one or more pores.

In one embodiment of the present invention, echogenic polymer microcapsules and/or nanocapsules are produced as follows. A non-water soluble substance which dissolves in a non-polar solvent and sublimes from a solid state is first dissolved in one or more volatile non-polar solvents to form a first mixture. Any non-water soluble substance which dissolves in a non-polar solvent and sublimes from a solid state can be used to produce this first mixture. Examples include but are not limited to, camphor, para-ph, camphene, naphthalene, cocoa butter and theobroma oil. Examples of non-polar solvents which can be used include, but are not limited to, methylene chloride, acetone, acetonitrile, tetrahydrofuran, chloroform, pentane, pentene, and methyl ethyl ketone. In a preferred embodiment, the non-water soluble substance is camphor and the solvent is methylene chloride. A preferred ratio of camphor to methylene chloride is 0.05 grams: 10 ml. Additional non-polar solvents from the above-listed examples can also be added to the mixture to control the size of the capsules in the nano size range (nanocapsules). Addition of a second, preferably different solvent reduces the size of the capsules because of its different properties. For example, the rate at which the solvent leaves the capsules during the hardening phase effects the size of the capsules. Specifically, the faster the solvent leaves the smaller the capsule. Acetone leaves the capsules faster than methylene chloride. Accordingly, addition of acetone as a second solvent results in nanosized capsules in comparison to the micronized capsules formed when using only methylene chloride.

For purposes of the present invention, by "nanocapsule" it is meant a capsule sufficiently small in size to access the microvasculature of the human body. Nanocapsules of the present invention range in size from about 10 nm to about 500 nm, while microcapsules of the present invention range in size from about 500 nm to about 1000 microns. Nanocapsules of this size provide an advantage in that they can access areas difficult if not impossible to reach with microcapsules. For example, nanocapsules can pass through leaky tumor vasculature. In addition, nanocapsules have different resonance frequencies thus providing advantages in both imaging and delivery of bioactive agents. Nanocapsules of the present invention have been found to be echogenic above 10 MHZ.

After the non-water soluble substance is fully dissolved in the non-polar solvent, a polymer material is added to the first mixture. Examples of polymers that can be used in this method include, but are not limited to, polylactide, a polyglycolide, a polycaprolactone, a copolymer of polylactide and polyglycolide, a copolymer of lactide and lactone, a polysaccharide, a polyanhydride, a polystyrene, a polyalkylcyanoacrylate, a polyamide, a polyphosphazene, a poly(methylmethacrylate), a polyurethane, a copolymer of methacrylic acid and acrylic acid, a copolymer of hydroxyethylmethacrylate and methylmethacrylate, a polyaminoacid, and a polypeptide. Preferred polymers are those which are biocompatible and/or biodegradable. In a preferred embodiment the polymer is polylactic co-glycolic acid (PLGA). In this embodiment it is preferred that 0.5 grams of the polymer be added to the 10 ml solution of the first mixture.

The polymer is then stirred into the first mixture until it is completely dissolved, thus forming the second mixture.

The second mixture is then emulsified either with or without water. For emulsification with water, an aliquot of distilled water, preferably 1 ml, is added to a second mixture comprising 10 ml of methylene chloride, camphor and PLGA, and a probe sonicator is used for 30 seconds. A similar emulsification procedure can be performed without the water. This emulsion of a second mixture of methylene chloride, camphor and PLGA produces a population of microcapsules that range in size from 0.1 to 1 mm. In the context of the present invention this population of microcapsules is referred to as the first population of microcapsules.

The first population of microcapsules is then poured into a surfactant and homogenized for several minutes. Examples of surfactant which can be used in the present invention include, but are not limited to, poly(vinyl) alcohol, Tweens and non-ionic surfactants. In a preferred embodiment, microcapsules of camphor and PLGA are added to 50 ml of a 5% polyvinyl alcohol (PVA) solution and homogenized for 5 minutes at 9,500 rpm. The addition of the surfactant allows for the breakup of the microcapsules into smaller beads to produce a second population of microcapsules and/or nanocapsules. This procedure enhances the size reduction of the microcapsules, an important step in the production process. In a preferred embodiment, the second population of microcapsules is poured into a hardening agent such as 100 ml of a 2% isopropanol solution and stirred for one hour. This removes residual methylene chloride and hardens the microcapsules. Alternatively, the isopropanol is poured into the container holding the microcapsules and stirred for one hour to remove residual methylene chloride and to harden the microcapsules. Examples of hardening agents that can be used include, but are not limited to, isopropanol, ethanol, methanol, ethyl ether, petroleum ether, heptane, and hexane.

Following this hardening step, the microcapsules are collected by centrifugation, washed with excess distilled water, centrifuged again, and washed multiple times with a solvent such as hexane which removes the non-water soluble substance without dissolving the polymer. Hexane also acts as a hardening agent removing the residual methylene chloride further drying the capsules. After each wash the wash solvent is removed by pipetting. A final washing with distilled water is then performed. The washed population of polymer microcapsules and/or nanocapsules are then centrifuged, frozen at −85° C., and then lyophilized to dry the capsules and remove any additional residual non-water soluble substance. This results in a free flowing powder of microcapsules and/or nanocapsules that is stable upon storage and can be resuspended routinely in a pharmaceutically acceptable vehicle such as saline just prior to use.

Particle size analysis of the final population of echogenic polymer microcapsules produced from camphor, methylene chloride and PLGA showed the population to be uniform in size with a range of 0.4 to 1.6 microns.

Acoustic dose-response experiments were performed using these echogenic polymer microcapsules. Four single element, broadband, 12.7 mm element diameter, 50.8 mm spherically focused transducers (Panametrics, Waltham, Mass.) with center frequencies of 2.25 MHZ, 5 MHZ, 7.5 MHZ and 10 MHZ, respectively, were chosen to represent the conventional medical ultrasound range. The 6 dB bandwidths of the transducers were 89%, 92%, 71% and 65% respectively. A known quantity (0.01 g to 1.0 g) of the echogenic polymer microcapsules was weighed into 50 ml of phosphate-buffered saline in a sample container and a dose-response was recorded. Doses on the dose-response curve were repeated six times. Fresh buffer was used at each dose and a 10 second delay post-administration of the agent in the container ensured proper mixing prior to collecting any signal. The signal was 2.0 micro seconds time-gated, after the ringing from the wall signal had subsided. The root mean square (rms) of the gated signal was calculated and the average for 50 A-lines with no agent was taken as baseline $s_0(t)$. Similarly, the average for 50 A-lines with contrast agent $s_{cA}(t)$ was calculated and presented relative to $s_0(t)$ as enhancement ($\Sigma E$) expressed in dB.

$$\Sigma E = 20 \log_{10} [rms(s_{CA}(t))/rms(s_0(t))]$$

The microcapsules of the present invention produced a dose-response relationship.

In another embodiment of the present invention, echogenic polymer microcapsules and/or nanocapsules can be produced in similar fashion to the above-described microcapsules with the following modifications. In the emulsification step, an agent which is dissolved in an aqueous solution and which sublimes is added. Examples of such agents which are water soluble and which sublime include, but are not limited to ammonium carbonate and other ammonium salts, theobromine and theobromine acetate. In a preferred embodiment, 1.0 ml of a 4% ammonium carbonate aqueous solution is added to the second mixture prior to probe sonication.

Size distribution analysis of these microcapsules via Coulter size analysis showed a mean diameter of 1.242 μm. Size distribution analysis of microcapsules via Horiba size analysis revealed a mean diameter of 1.210 μm.

The polymer microcapsules prepared in accordance with this method using camphor and ammonium carbonate were echogenic and an in vitro dose response was shown to be related to the frequency at which the capsules were insonated giving an enhancement of 14.8, 25.4, 25.3 and 20.8 dB when insonated with 2.25, 5, 7.5, and 10 MHZ ultrasound energy, respectively, for a dose of only 8 μg of microcapsules/ml of buffer (approximately $1.6 \times 10^6$ microbubbles per ml). This dose is relatively low in comparison to the 6 mg/ml dose required to achieve a 23 dB enhancement from microcapsules wherein only camphor was encapsulated and sublimed. Thus, microcapsules prepared in accordance with this method wherein ammonium carbonate, an agent that is soluble and sublimes, is dissolved in an aqueous solution and added prior to emulsification, require a lower dose to give the same acoustic enhancement as microcapsules prepared without this additional step.

A shadowing effect was also observed with the microcapsules.

In vivo power Doppler imaging was also performed in New Zealand White rabbits using these microcapsules as the imaging agent and showed enhancement of the image in comparison to imaging taken without the agent. In vivo dose response curves showed a significant acoustic enhancement of up to 24 dB, with a dose of 0.15 mL/kg.

Thus, as demonstrated herein, echogenic polymer microcapsules and nanocapsules produced in accordance with these methods can be used for imaging of any of the various tissues and epithelium and/or endothelium thereof routinely imaged with ultrasound techniques including, but not limited to, renal tissue, brain tissue, tumor vasculature, skin tissue, pancreatic tissue, breast tissue, heart tissue, prostate tissue, uterine tissue, adrenal gland tissue, retinal tissue, muscle tissue, areas of plaque and areas of ischemia.

For use as a contrast agent, it is preferred that the echogenic microcapsules and/or nanocapsules of the present invention be hollow or porous so that they can be filled with gas. Such gas-filled polymer microcapsules are produced by introducing echogenic hollow or porous polymer microcapsules into contact with a gas and equilibrating the microcapsules with the gas for a period of time sufficient to allow diffusion of the gas into the polymer microcapsules, resulting in a gas-filled polymer microcapsule. This procedure of exposing hollow or porous polymer microcapsules to the gas may be carried out at ambient pressure (atmospheric), at subatmospheric pressure, or at an elevated pressure. The period of time required to effect filling of the hollow microcapsules with the gas is relatively short, typically requiring only a few minutes, the actual time depending on the manner and pressure at which the hollow microcapsules are equilibrated with the gas. The term "gas" as used in this specification includes substances which are in gaseous form under normal storage conditions, e.g., at about 15 to 25° C., and/or at normal mammalian body temperature, e.g., 37° C. in humans. The resulting gas-filled polymer microcapsules of this invention may be stored as a dry, free-flowing powder, preferably in the presence of the gas contained in the polymer microcapsules.

The gas-filled microcapsules are useful as contrast agents in medical imaging, such as diagnostic ultrasound. Ultrasound contrast compositions typically comprise the hollow or porous polymer microcapsules, filled with a gas, and dispersed in an aqueous liquid which serves as a carrier for the contrast agent. Aqueous liquids that can be used include, but are not limited to, isotonic saline and phosphate-buffered saline. The contrast agent composition is then injected into the bloodstream and used for ultrasound visualization of specific blood vessels or body organs.

The polymer microcapsules and nanocapsules of the present invention can be used for delivery of bioactive agents. In this embodiment, a bioactive agent may be adsorbed to and/or attached to the surface of the microcapsule or nanocapsule. To adsorb a drug product to the microcapsule surfaces, the drug is dissolved in distilled water or a buffer, and then the dried microcapsules are suspended in distilled water with the drug. The suspension is stirred overnight and then the suspension centrifuged to collect capsules. The resulting microcapsules are then washed, frozen and lyophilized. The lyophilized microcapsules have the drug product to be delivered adsorbed to their surfaces. Bioactive agents can also be attached to the microcapsules and/or nanocapsules in accordance with well known methods for conjugation. For example, a conjugation method such as taught in Example 8 may be used substituting the bioactive agent for the ROD peptide. Alternatively, or in addition, a bioactive agent can be encapsulated in the microcapsule or nanocapsule. Water soluble bioactive agents can be encapsulated in the microcapsules or nanocapsules by including water during emulsification and dissolving the bioactive agent in this water. Non-water soluble bioactive agents can be encapsulated in the microcapsules or nanocapsules by dissolving the bioactive compound in the non-polar organic solvent in the first step of preparation of these capsules. Examples of bioactive agents which can be adsorbed, attached and/or encapsulated in the microcapsules and/or nanocapsules of the present invention include, but are not limited to, antineoplastic and anticancer agents such as azacitidine, cytarabine, fluorouracil, mercaptopurine, methotrexate, thioguanine, bleomycin peptide antibiotics, podophyllin alkaloids such as etoposide, VP-16, teniposide, and VM-26, plant alkaloids such as vincristine, vinblastin and paclitaxel, alkylating agents such as busulfan, cyclophosphamide, mechlorethamine, melphanlan, and thiotepa, antibiotics such as dactinomycin, daunorubicin, plicamycin and mitomycin, cisplatin and nitrosoureases such as BCNU, CCNU and methyl-CCNU, anti-VEGF molecules, gene therapy vectors and peptide inhibitors such as MMP-2 and MMP-9, which when localized to tumors prevent tumor growth.

Once prepared, microcapsules and/or nanocapsules comprising the bioactive agent can be suspended in a pharmaceutically acceptable vehicle for injection into animals, including humans. Once injected, the bioactive agent is released by either biodegradation over time of the polymer microcapsule structure, by initiation of release of the bioactive agent through exposure to ultrasound, or by a combination thereof.

Compositions of the present invention can be used to direct delivery of a bioactive agent to any of the various tissues and epithelium and/or endothelium thereof including, but not limited to, renal tissue, lung tissue, brain tissue, tumor vasculature, skin tissue, pancreatic tissue, breast tissue, heart tissue, prostate tissue, intestinal tissue, uterine tissue, adrenal gland tissue, retinal tissue, muscle tissue, areas of plaque, areas of inflammation, and areas of ischemia.

The microcapsules and/or nanocapsules of the present invention may further comprise a targeting agent attached to the capsule surface which upon systemic administration can target the contrast agent or the delivery agent to a selected tissue or tissues, or cell in the body. Targeting agents useful in the present invention may comprise peptides, antibodies, antibody fragments, or cell surface receptor-specific ligands that are selective for a tissue or cell. Examples include, but are in no way limited to, RGD which binds to αv integrin on tumor blood vessels, NGR motifs which bind to aminopeptidase N on tumor blood vessels and ScFvc which binds to the EBD domain of fibronectin. Accordingly, targeting agents can be routinely selected so that a contrast agent or delivery agent of the present invention, or a combination thereof, is directed to a desired location in the body such as selected tissue or tissues, cells or an organ, or so that the contrast agent or delivery agent of the present invention can distinguish between various tissues such as diseased tissue versus normal tissue or malignant tissue versus benign tissue. Targeted contrast and/or delivery agents can be administered alone or with populations of contrast agents and/or delivery agents of the present invention which do not further comprise a targeting agent.

RGD peptide was conjugated to echogenic polymer microcapsules of the present invention. The microcapsules were coated with an ROD peptide that targets integrins specific to angiogenesis, αvβ3 and αvβ5. The microcapsules were then bound to rat neuroblastoma cells in vitro within 6 hours. The results of this study demonstrate that microspheres bound to a selected targeting agent can be used to target selected cells. Such microcapsules are useful for targeted imaging, targeted therapeutic imaging and delivery of bioactive agents using the microspheres of the present invention as the vehicle.

The following nonlimiting examples are provided to further illustrate the present invention.

EXAMPLES

Example 1

Materials

Poly (D,L-lactide-co-glycolic acid 50:50, PLGA) (Medisorb 5050 DL 3A, lot 1010-412) was purchased from Alkermes. Poly (vinyl alcohol) (PVA), 88% mole hydrolyzed, with a $M_w$ of 25,000 was purchased from Polysciences, Inc. (1R)-(+)-Camphor, Ammonium Dihydrogen Phosphate, GRGDS (Gly-Arg-Gly-Asp-Ser) peptide complex, EDC (1-Ethyl-3,-3-Dimethylamino-Propyl) carbodiimide, NHS (N-Hydroxysulfosuccinimide), Antibiotics (penicillin and streptomycin), and L-glutamine were from Sigma. Dulbecco's Modified Eagle Medium (DMEM), Hank's Balanced Salt Solution, and Fetal Bovine Serum (PBS) were purchased from Fisher. Ammonium Carbonate was purchased from J. T. Baker. All other chemicals were reagent grade from Fisher.

Example 2

Production of Camphor Containing Microcapsules

Camphor (0.05 g) and PLGA (0.5 g) were dissolved in 10 ml of methylene chloride and probe sonicated at 117 Volts for 30 seconds. The resulting emulsion was then poured into a 5% PVA solution and homogenized for 5 minutes at 9,500 rmp. The homogenate was then poured into a 2% isopropanol solution and stirred for 1 hour. The capsules were collected by centrifugation, washed three times with hexane, then once with deionized water and lyophilized, using a Virtis Benchtop freeze dryer, to remove the camphor core.

Example 3

Preparation of Camphor and Ammonium Carbonate Containing Microcapsules

Camphor (0.05 g) and PLGA (0.5 g) were dissolved in 10 ml of methylene chloride. 1.0 ml of 4% ammonium carbonate solution was added to the polymer solution and probe sonicated at 117 Volts for 30 seconds. The emulsion was then poured into a 5% PVA solution and homogenized for 5 minutes at 9,500 rmp. The homogenate was then poured into a 2% isopropanol solution and stirred for 1 hour. The capsules were collected by centrifugation, washed three times with hexane, then once with deionized water and lyophilized, using a Virtis Benchtop freeze dryer, to remove the camphor and ammonium carbonate core.

Example 4

Size Distribution

Static light scattering using a Horiba LA-910 Particle Size Analyzer (Horiba Instrument) and Coulter Multisizer II were used and compared to measure the size distribution of the capsules.

Example 5

Scanning Electron Microscopy (SEM)

Scanning electron micrographs, (using an Amray model 1830D SEM) were taken of the freeze dried capsules. The capsules were mounted on metal stubs with double sided electrical tape. They were gold coated and viewed under the SEM.

Example 6

In Vitro Acoustic Studies

The freeze-dried capsules were weighed into a 100 ml custom-made vessel equipped with an acoustic window, and 50 ml of phosphate buffered saline (PBS) solutions were added. The suspension was then placed in the acoustic set-up and sonicated using transducers with varying center frequencies, 2.25, 5, 7.5 and 10 MHZ. The acoustic enhancement was analyzed using Lab View. Dose response curves were constructed for doses in the range of 0 mg/ml to 12 µg/ml, from readings taken within the first 30 seconds.

Example 7

In Vivo Acoustic Studies

All in vivo studies were performed on New Zealand white rabbits of either sex, within the weight range of 2.0 to 5.0 kg. The rabbits were sedated with an intramuscular injection of 0.65 mg/ml of Ketamine hydrochloride (Ketaset, Aveco) and xylazine hydrochloride (Gemimi). After each experiment the rabbit was sacrificed by a lethal dose of pentobarbital (Beuthanasia). The agent was weighed and suspended in saline prior to injection. The agent was injected through a catheterized ear vein using an 18-gauge needle. Immediately after injection the injection port was flushed with 5 cc saline. Power Doppler imaging of the kidney was performed using an abdominal scan.

In vivo dose response curves were constructed in different rabbits. A custom made Silex 10 MHZ cuff transducer was placed around the distal aorta below the renal arteries, which was exposed surgically prior to the experiment. This setup reduced interference and noise from respiratory movements. A pulsed Doppler instrument (SDD 600; Vingmed Sound, Oslo, Norway) recorded the quadrate audio outputs. The contrast enhancement (in dB) was calculated by a known technique from the recorded data, the change in power over time.

Example 8

Coating of Microcapsules with ROD Peptide

Dried microcapsules (100 mg) were combined with 5 mg 1-ethyl-3-(dimethylamino-propyl)-carbodiimide (EDC) (1:1 mole ratio of COOH groups), 1.4 mg of N-hydroxysuccinimide (NHS) (1:2 mole ratio to EDC), in 10 ml of buffer (0.1 M MES, 0.3 M NaCl, pH 6.5) and stirred for 15 minutes. RGD peptide (150 µg) was then added and stirred for 24 hours. The microcapsules were washed with deionized water three times and lyophilized.

Example 9

Cell Culture

The NB2A mouse neuroblastoma cells were cultured using growth medium containing 90% DMEM, 10% FBS, and 2 mM L-glutamine. The medium was changed and the cells were split every three days. The experiment was performed on the cells at passage 10.

Example 10

Microcapsule Attachment

Cells were plated in each well of a 12-well cell culture plate along with 3 ml of growth medium. After three days, the cells became confluent and the growth medium was changed. The cells were then washed with Hank's salt solution and replaced with a modified medium containing microcapsules, either PLGA with or without RGD peptide, suspended in the growth medium at a concentration of 0.5 mg/ml. The cells were then incubated for 0, 1, and 6 hours. After each specified time point, the medium was removed and the cells were washed again with Hank's salt solution.

The cells were then viewed under a Wesco Verta 7000 series microscope. Digital pictures were taken using an Olympus DP11 digital camera interfaced with the microscope at a magnification of 625x.

What is claimed is:

1. An echogenic polymer microcapsule or nanocapsule comprising:
   (a) a hardened outer surface consisting of (1) a hardened non water soluble polymer and (2) pores in the hardened outer surface of the microcapsule or nanocapsule formed by removal of a non-water soluble sublimable substance; and
   (b) a hollow core formed by removal of a water soluble sublimable substance, wherein said hollow core is encapsulated by the hardened outer surface, wherein said echogenic polymer microcapsule or nanocapsule is made from (i) an outer surface forming mixture consisting of a non water soluble polymer and the non-water soluble sublimable substance dissolved in one or more volatile non-polar solvents and (ii) an inner surface forming mixture comprising the water soluble sublimable substance dissolved in water;
   wherein said microcapsule or nanocapsule has a diameter from about 400 nanometers to about 1.6 microns.

2. An echogenic polymer microcapsule or nanocapsule comprising:
   (a) a hardened outer surface consisting of (1) a hardened non water soluble polymer and (2) pores in the hardened outer surface of the microcapsule or nanocapsule formed by removal of a non-water soluble sublimable substance; and
   (b) a hollow core formed by removal of a water soluble sublimable substance, wherein said hollow core is encapsulated by the hardened outer surface, wherein said echogenic polymer microcapsule or nanocapsule is made from (i) an outer surface forming mixture consisting of a non water soluble polymer and the non-water soluble sublimable substance dissolved in one or more volatile non-polar solvents and (ii) an inner surface forming mixture comprising the water soluble sublimable substance dissolved in water;
   wherein said microcapsule or nanocapsule has an in vitro dose response of at least 14.8 dB for a dose of 8 micrograms per milliliter ($\mu$g/ml) buffer when insonated at 2.25 MHz.

3. A contrast agent for diagnostic imaging in a patient comprising echogenic polymer microcapsules or nanocapsules having (a) a hardened outer surface consisting of (1) a hardened non water soluble polymer and (2) pores in the hardened outer surface of the microcapsule or nanocapsule formed by removal of a non-water soluble sublimable substance; and (b) a hollow core filled with a gas, on the condition that a dose of 8 $\mu$g/ml of said echogenic polymer microcapsules or nanocapsules provides an enhancement of 14.8 to 25.4 dB for an ultrasound image when insonated with 2.25 to 10 MHz ultrasound energy.

4. A method for imaging a tissue or tissues in a subject, said method comprising parenterally administering to the subject a contrast agent comprising echogenic polymer microcapsules or nanocapsules having (a) a hardened outer surface consisting of (1) a hardened non water soluble polymer and (2) pores in the hardened outer surface of the microcapsule or nanocapsule formed by removal of a non-water soluble sublimable substance; and (b) a hollow core filled with a gas, on the condition that a dose of 8 $\mu$g/ml of said echogenic polymer microcapsules or nanocapsules provides an enhancement of 14.8 to 25.4 dB for an ultrasound image when insonated with 2.25 to 10 MHz ultrasound energy.

5. A method for selectively imaging a tissue or tissues in a subject said method comprising parenterally administering to the subject a contrast agent comprising echogenic polymer microcapsules or nanocapsules having (a) a hardened outer surface consisting of (1) a hardened non water soluble polymer and (2) pores in the hardened outer surface of the microcapsule or nanocapsule formed by removal of a non-water soluble sublimable substance; and (b) a hollow core filled with a gas, on the condition that a dose of 8 $\mu$g/ml of said echogenic polymer microcapsules or nanocapsules provides an enhancement of 14.8 to 25.4 dB for an ultrasound image when insonated with 2.25 to 10 MHz ultrasound energy said contrast agent further comprising a targeting agent attached to an outer surface of the microcapsules or nanocapsules.

6. A method for selectively imaging a tissue or tissues in a subject, said method comprising parenterally administering to a subject a contrast agent comprising echogenic polymer microcapsules or nanocapsules having (a) a hardened outer surface consisting of (1) a hardened non water soluble polymer and (2) pores in the hardened outer surface of the microcapsule or nanocapsule formed by removal of a non-water soluble sublimable substance; and (b) a hollow core with a gas, on the condition that a dose of 8 $\mu$g/ml of said echogenic polymer microcapsules or nanocapsules provides an enhancement of 14.8 to 25.4 dB for an ultrasound image when insonated with 2.25 to 10 MHz ultrasound energy said contrast agent further comprising a targeting agent attached to an outer surface of the microcapsules or nanocapsules, wherein said contrast agent selectively targets diseased tissue and distinguishes the diseased tissue from normal tissue.

7. A method for selectively imaging a tissue or tissues in a subject, said method comprising parenterally administering to the subject a contrast agent comprising echogenic polymer microcapsules or nanocapsules having (a) a hardened outer surface consisting of (1) a hardened non water soluble polymer and (2) pores in the hardened outer surface of the microcapsule or nanocapsule formed by removal of a non-water soluble sublimable substance; and (b) a hollow core filled with a gas, on the condition that a dose of 8 $\mu$g/ml of said echogenic polymer microcapsules or nanocapsules provides an enhancement of 14.8 to 25.4 dB for an ultrasound image when insonated with 2.25 to 10 MHz ultrasound energy said contrast agent further comprising a targeting agent attached to an outer surface of the microcapsules or nanocapsules, wherein the contrast agent selectively targets malignant tissue and distinguishes the malignant tissue from benign tissue.

8. A method of imaging tissues in a subject, wherein the vasculature of said tissues are too narrow for access by microcapsules, said method comprising parenterally administering to the subject a contrast agent comprising echogenic polymer nanocapsules having (a) a hardened outer surface consisting of (1) a hardened non water soluble polymer and (2) pores in the hardened outer surface of the nanocapsule formed by removal of a non-water soluble sublimable substance; and (b) a hollow core filled with a gas, on the condition that a dose of 8 $\mu$g/ml of said echogenic polymer nanocapsules provides an enhancement of 14.8 to 25.4 dB for an ultrasound image when insonated with 2.25 to 10 MHz ultrasound energy, wherein said echogenic nanocapsules are filled with a gas.

9. A composition for delivery of a bioactive agent comprising an echogenic polymer microcapsule or nanocapsule of claim 2 and a bioactive agent adsorbed to, attached to, encapsulated in, or any combination thereof, the echogenic polymer microcapsule or nanocapsule.

10. The composition of claim 9 further comprising a targeting agent attached to an outer surface of the microcapsule or nanocapsule.

11. The composition of claim 9 comprising an echogenic polymer nanocapsule.

12. A method for delivering a bioactive agent to a subject comprising administering to the subject the composition of claim 9 and triggering release of the bioactive agent in the subject by ultrasound.

13. A method for delivering a bioactive agent to a subject comprising administering to the subject the composition of claim 12 wherein bioactive agent is released by degradation of the echogenic polymer microcapsule or nanocapsule.

14. The method of claim 13 wherein degradation of the echogenic polymer microcapsule or nanocapsule and release of the bioactive agent is altered by ultrasound.

15. A method for targeting a bioactive agent to a selected tissue in a subject comprising administering to the subject the composition of claim 10.

16. The method of claim 15 wherein the composition is targeted to diseased tissue.

17. The method of claim 15 wherein the composition is targeted to malignant tissue.

18. A method of delivering a bioactive agent to tissues in subject via vasculature too narrow for access by microcapsules comprising administering to the subject the composition of claim 11.

19. The echogenic polymer microcapsule or nanocapsule of claim 12, wherein the non-water soluble polymer is a member selected from the group consisting of polylactide, polyglycolide, a copolymer of lactide and lactone, a polyanhydride, a polystyrene, a polyalkylcyanoacrylate, a polyamide, a polyphosphazene, a poly(methylmethacrylate), a polyurethane, a copolymer of methacrylic acid and acrylic acid, and a copolymer of hydroxyethylmethacrylate and methylmethacrylate.

20. A echogenic polymer microcapsule or nanocapsule comprising:
  (a) a hardened outer surface consisting of a hardened non water soluble polymer; and
  (b) a core encapsulated within the hardened non-water soluble polymer comprising a gas, wherein said echogenic polymer microcapsule or nanocapsule has an in vitro dose response of enhancement of at least 14.8 dB for an ultrasound image when insonated with 2.25 to 10 MHz ultrasound energy at a dose of about 8 µg/ml, and has a shadowing effect.

21. The echogenic microcapsule or nanocapsule of claim 2, wherein said microcapsule or nanocapsule has a diameter of about 400 nanometers to about 1.6 microns.

22. The contrast agent of claim 3, wherein said microcapsules or nanocapsules have a diameter of about 400 nanometers to about 1.6 microns.

23. The method of claim 4, wherein said microcapsules or nanocapsules have a diameter of about 400 nanometers to about 1.6 microns.

24. The method of claim 5, wherein said microcapsules or nanocapsules have a diameter of about 400 nanometers to about 1.6 microns.

25. The method of claim 6, wherein said microcapsules or nanocapsules have a diameter of about 400 nanometers to about 1.6 microns.

26. The method of claim 7, wherein said microcapsules or nanocapsules have a diameter of about 400 nanometers to about 1.6 microns.

27. The method of claim 8, wherein said nanocapsules have a diameter of about 10 nanometers to about 500 nanometers.

28. The echogenic polymer microcapsule or nanocapsule of claim 20, wherein said microcapsule or nanocapsule has a diameter of about 400 nanometers to about 1.6 microns.

\* \* \* \* \*